United States Patent [19]

Buma

[11] Patent Number: 5,092,850

[45] Date of Patent: Mar. 3, 1992

[54] CATHETER WITH ADJUSTABLE EXTERNAL LOCKING BOLSTER

[76] Inventor: Shelley J. Buma, 218 Hill St., Whitinsville, Mass. 01588

[21] Appl. No.: 619,762

[22] Filed: Nov. 29, 1990

[51] Int. Cl.⁵ .................................. A61M 5/32
[52] U.S. Cl. .................................. 604/175; 604/178; 604/256
[58] Field of Search ............... 604/174, 175, 177, 178, 604/179, 93, 247, 280, 256, 263, 264, 104; 600/32

[56] References Cited

U.S. PATENT DOCUMENTS

| | | | |
|---|---|---|---|
| 3,856,021 | 12/1974 | McIntosh | 604/175 |
| 4,217,664 | 8/1980 | Faso | 600/32 |
| 4,863,438 | 9/1989 | Gauderer et al. | 604/175 |
| 4,944,732 | 7/1990 | Russo | 604/175 |
| 5,007,900 | 4/1991 | Picha et al. | 604/106 |

Primary Examiner—Gene Mancene
Assistant Examiner—Michael Lynch
Attorney, Agent, or Firm—Blodgett & Blodgett

[57] ABSTRACT

A catheter with an adjustable, external locking bolster. The catheter is for insertion into a body and includes a distal tip which is positioned inside the body, and a tubular member which is in communication with the distal tip. A portion of the tubular member exists outside the body and is provided on its outer surface with engagement elements. An external coupling has matching engagement elements for selective, adjustable securement to the tubular member. A compression element is provided which locks the external coupling to the tubular element and prevents slippage. The adjustable engagement allows a low profile, close to the skin appearance, while the compression element securely locks the external coupling to the tubular member.

30 Claims, 2 Drawing Sheets

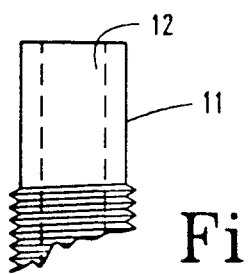
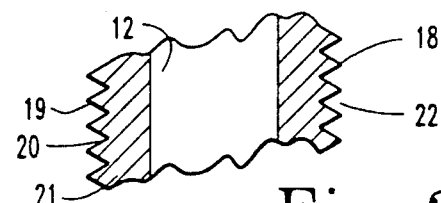
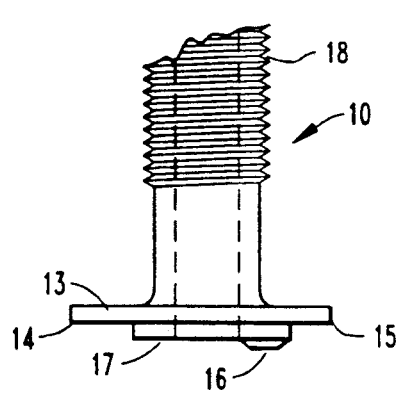
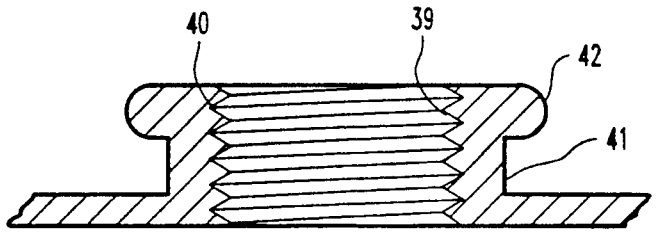
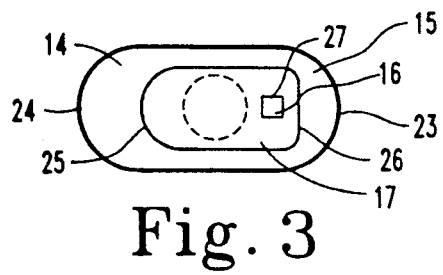
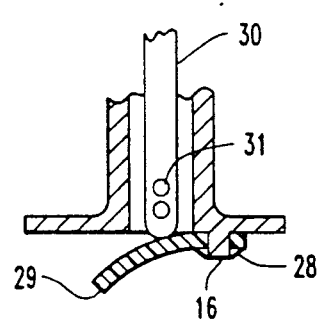
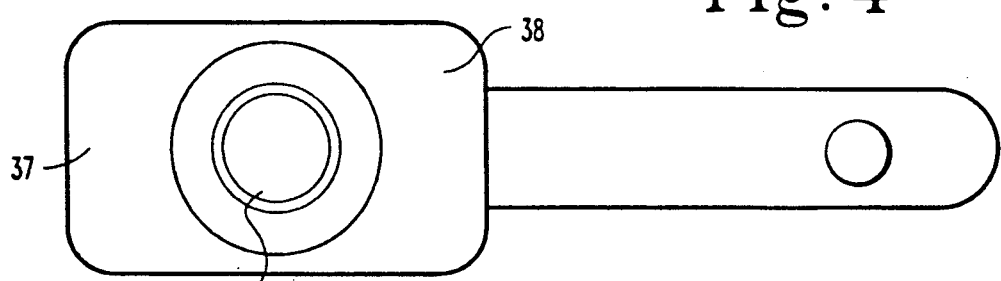
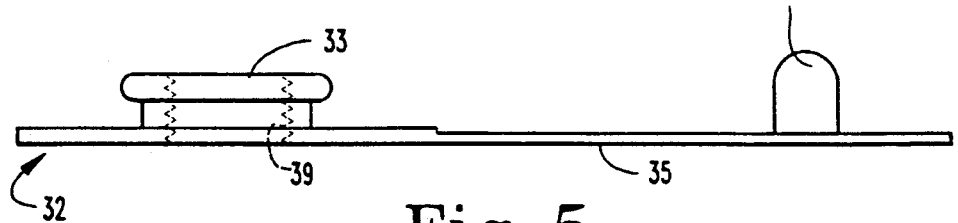

CATHETER WITH ADJUSTABLE EXTERNAL LOCKING BOLSTER

BACKGROUND OF THE INVENTION

The use of various indwelling catheters, especially feeding devices, is well known in the medical art. Feeding tubes may be left in place within the body for a considerable period of time, often up to a year. This is possible due to the use of recent advancements in biocompatible materials, especially silicone indwelling devices which permit long term placement of a device without body rejection or tissue reaction.

Medical grade silicone devices are routinely used in gastrostomy feeding devices as well as other types of devices such as wound drains and infusion catheters. The silicone material has many biocompatibility advantages including the ability to remain soft and flexible for long periods of time within the body.

Feeding devices and catheters made from silicone are molded, extruded, and assembled such that the silicone material is very smooth and the surface finish has a very low coefficient of friction. The surface of the silicone catheter becomes very slippery especially when it is in contact with body fluids.

To prevent inward migration of the catheter, designers and manufactures have added external retention devices to their products. Silicone retention discs are manufactured in various sizes to stabilize catheters and are produced by such companies as Wilson-Cook.

Gastrostomy feeding devices are also available from C. R. Bard, Ross Laboratories, and Superior Biosystems (manufactured for Sandoz Nutrition Inc.) with pre-loaded retention discs already on the catheter.

Low profile gastrostomy ports of fixed lengths are also produced by these three manufacturers, and are available in various sizes and lengths with molded in external bolsters to prevent tube migration.

The problem with the retention discs is that they easily slide on the tubular shaft of the catheter and the catheter easily migrates inside the body.

If the gastrostomy devices has an inner balloon then the ballon can block internal body passageways and cause an obstruction if the retention disc fails. This is often the case.

To prevent disc slippage, pull ties have been added to the disc. However, the disc still often fails due to the smooth slippery outer surface of the catheter and the smooth inner surface of the molded retention disc.

The low profile gastrostomy devices from C. R. Bard, Ross, or Superior must be molded with fixed lengths which means extra devices to measure the lengths of patients' stoma tracts and the added inventory and expense of many different fixed lengths and sizes.

The low profile devices of Gauderer U.S. Pat. No. 4,863,438 and Russo U.S. Pat. No. 4,944,732 all show fixed lengths.

The low profile devices of Gauderer and Russo have many advantages, however, many hospitals do not use these devices because of the large inventory of different sizes and lengths required, and the frustration of doctors and nurses in selecting the right size. Even with all the sizes available, some patients cannot be fit with a low profile device because the correct length is not available.

Manufacturing and inventory costs of the low profile devices make them very expensive for most patients and hospitals.

BRIEF SUMMARY AND OBJECTIVES OF THE INVENTION

With the foregoing in mind, the present invention offers all the advantages of the prior art with additional features and at a lower cost.

The present invention has an infinitely adjustable external bolster to prevent inward tube migration and can be locked in place to eliminate tube slippage.

Accordingly, it is primary objective to provide a device which is safer, more convenient to use, and less expensive than the devices presently manufactured.

An objective is to provide an external bolster which can be easily positioned by the physician.

Another objective is to provide an external bolster which can be locked in place after being positioned by the physician.

Another objective is to have the bolster, after locking it in place, become unitized on the catheter such that the catheter cannot move inward inside the body.

Another objective is to have the bolster with external flanges to further prevent tube migration after the bolster is permanently positioned on the catheter.

Another important objective is to provide a low profile, close to the skin surface catheter device which can be infinitely adjustable as to lengths desired inside the body.

Another objective is to provide a low profile gastrostomy feeding port close to the skin surface which is infinitely adjustable to fit any length of stoma tract.

Another objective is to eliminate the need for stoma tract length measuring devices in low profile gastrostomy feeding ports.

Another important objective is to provide a low profile, close to the skin surface gastrostomy device which can be placed for the first time in a patient using the percutaneous endoscopic gastrostomy technique.

Another objective is to provide a replacement low profile, close to the skin surface gastrostomy device which can be easily inserted and adjusted to the stoma tract length.

DESCRIPTION OF THE DRAWINGS

The following drawings illustrates the best mode presently contemplated for carrying out the invention.

FIG. 1 is a side-view of a tubular catheter including engagement elements on its outside diameter, a flexible tip with an anti-reflux valve shown normally closed.

FIG. 2 is an enlarged partial sectional view of the engagement elements.

FIG. 3 is an underside view of the flexible tip with the anti-reflux valve.

FIG. 4 is a partial sectional side view of the flexible tip with the anti-reflux valve shown opened by a rounded tip drainage catheter.

FIG. 5 is a side-view of the external bolster showing internal engagement elements and a closure cap.

FIG. 6 is a top-view of the external bolster.

FIG. 7 is a partial sectional enlarged view of the internal engagement elements.

DESCRIPTION OF THE INVENTION

Figure 8:
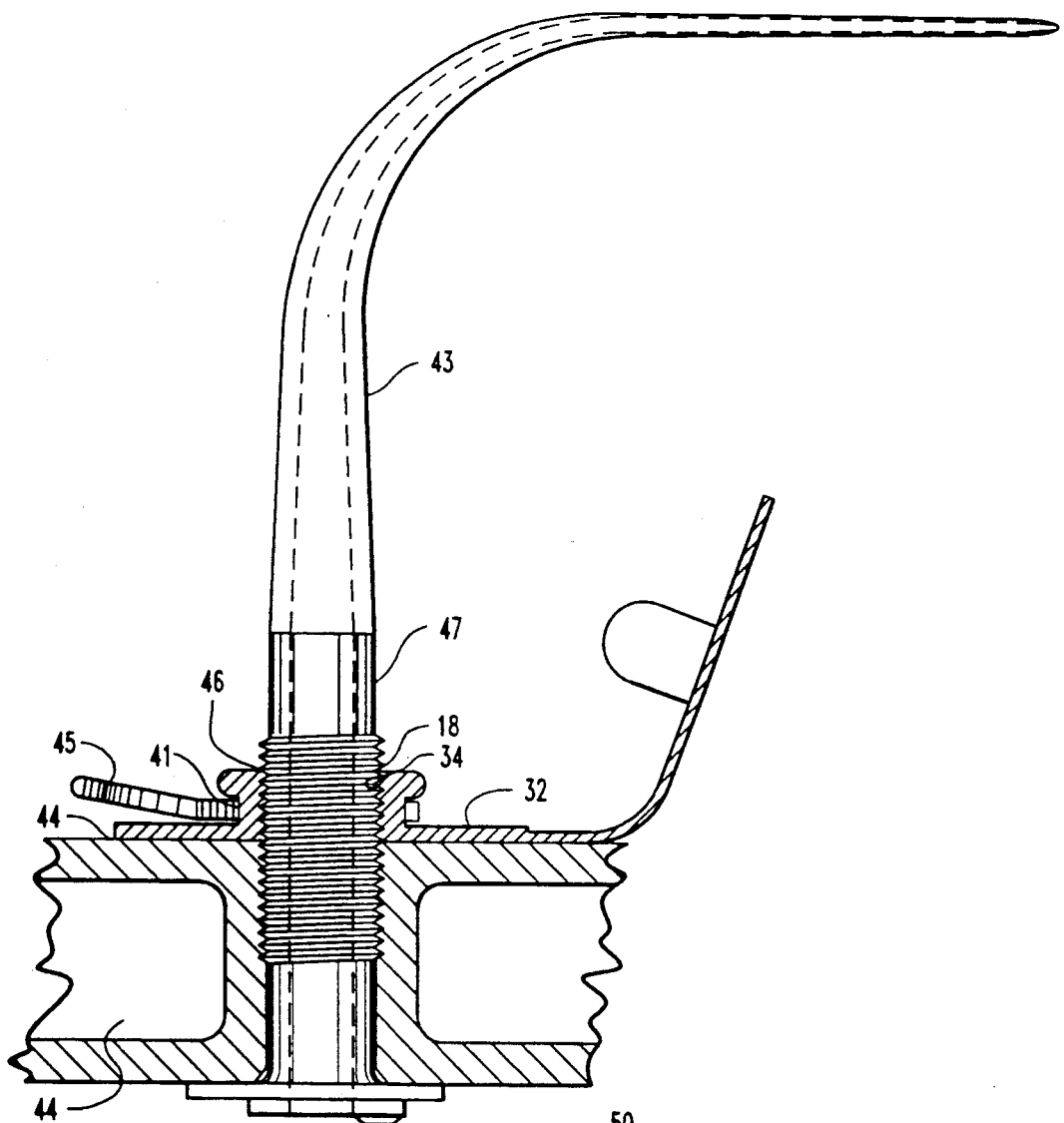
FIG. 8 is a sectional view of the catheter after placement in a body cavity showing it pre-assembled to a dilator, with the external bolster adjusted down close to the skin surface and a compression pull tie securing the engagement elements.

FIG. 1 shows molded catheter 10 which is tubular in shape with outside wall 11 and inside lumen 12. Lumen 12 extends the full length of the catheter.

The catheter can be molded from medical grade silicone either by compression or the liquid injection molding process.

A small percentage, about 5%, Barium can be formulated within the silicone to make the device radiopaque.

Distal tip 13 is integrally molded as part of the tubular catheter.

The tip has outwardly extending flanges 14 and 15.

Protruding downward and moded into the tip is square shaped lug 16.

Separately silicone moded anti-reflux valve 17 is of the flapper type.

Externally molded onto the outside wall 11 is a series of saw tooth rings 18 which are molded around the entire circumference of the outside wall 11.

The saw tooth rings 18 should begin with ½ inch of the distal tip and extend proximally along the catheter for a length of at least 3 inches.

FIG. 2 is an enlarged sectional view of the saw tooth rings 18.

The crest of the tooth 19 is the same dimension for all crested teeth.

The valley 20 of the tooth is also the same dimension for all valleys portions of the tooth.

The width of the tooth at its base 21 is about 0.050 inches and the height of each tooth 22 from valley to crest is also 0.050 inches Inside lumen 12 is molded smooth.

FIG. 3 which shows the underside of the distal tip shows flanges 14 and 15 with rounded edges 23 and 24.

Anti-reflux flapper valve 17 is molded flat with a rounded forward edge 25 and rearward straight edge 26.

A square shaped hole 27 is molded into the valve to mate with square shaped lug 16 on the distal tip.

FIG. 4 shows lug 16 extending slightly beyond the valve surface so that liquid silicone adhesive 28 can adhesive bond that lug to valve.

Square lug 16 both positions and correctly aligns the valve in place and acts as an adhesive lug.

Rounded edge 25 is free to flap open as in 29.

A hollow drainage obturator which is semi-rigid extruded and molded of PVC plastic can easily open flap valve 17 to drain or decompress a body cavity. Side drainage holes 31 can be positioned at the obturator tip.

FIG. 5 shows a side view of external bolster 32 which is also molded of silicone rubber.

The bolster has a molded in opening with internal saw teeth rings 34 which match external saw teeth rings 18 on the tubular shaft of catheter 10.

Extending off to one side of bolster 33 is a molded in strap 35 with a male closure plug 36.

FIG. 6 is a top view of the bolster which shows outward flanges 37 and 38.

FIG. 7 is an enlarged partial sectional view of the bolster in the saw teeth area.

The internally molded saw teeth have corresponding crests 39 and valleys 40 to crests 19 and valleys 20 as shown in FIG. 2.

The body of the bolster has a recessed groove 41 which runs around the entire outside surface of the bolster.

Above groove 41 is a projected annular ring 42.

FIG. 8 shows the catheter after placement within the body.

If the catheter were to be used as a gastrostomy feeding device it can be placed using the standard percutaneous endoscopic technique using either the "push" method or the "pull" method.

Attached to the proximal end of the catheter can be a long tapered dilator 43 which facilitates placement using the endoscopic technique.

The catheter is placed through the stomach wall 44.

Bolster 32 is slid over dilator 43 and ratchets down over saw teeth 18 on the catheter shaft.

Matching internal saw teeth 34 engage with saw teeth 18.

In practice, the external bolster can ratchet down 0.050 inches at a time for an infinitely precise fit down to skin surface 44.

Flanges 37 and 38 on the bolster can rest gently on the skin surface 44.

If the bolster is too tight down on the skin surface, it can be retracted upward by grabbing projected ring 42.

The bolster can be adjustable in either upward or downward movement on the tubular shaft in precise 0.050 inch increments.

Once in position, nylon pull tie 45 can be compressed securely into recessed ring 41 on the bolster.

The pull tie compresses the internal saw teeth on the bolster to permanently lock the matching teeth in place.

Once compressed, the crests and valleys of the teeth cannot move out of position and the bolster is securely locked onto the catheter shaft.

Pull tie 45 is of the one-way compression engagement nylon molded type.

Once pulled tight it cannot be retracted.

After securing the pull tie the catheter is carefully trimmed at surface 46 to remove excess tube 47 and dilator 43.

Figure 9:
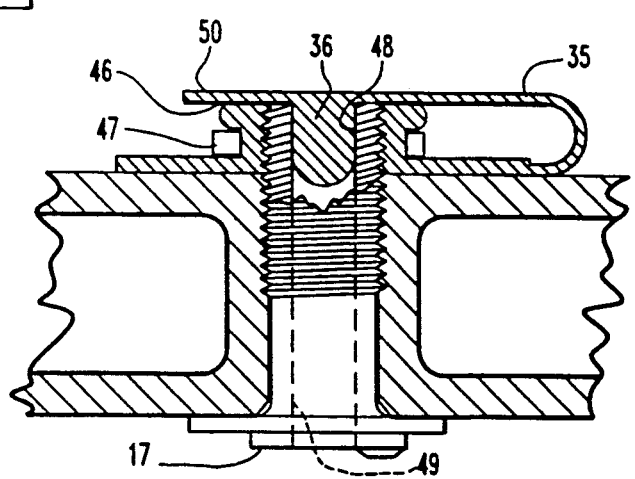
FIG. 9 is a sectional view of the catheter in a body cavity after the dilator and compression pull tie have been trimmed away, with the closure cap in place with the device shown in a low profile, close to the skin surface mode.

FIG. 9 shows a cross sectional view of the device in its final form after placement and in its low profile, close to the skin surface look.

After trimming the catheter at surface 46 the pull tie is also trimmed back to point 47 for a neat appearance.

The catheter lumen is fully open at point 48 and extends the full length to outward opening 49 at the distal tip.

Closure plug 36 will fit directly into lumen 46 at point 48.

The device now becomes a complete easy to place, low profile, close to the skin surface portal device.

The cap can be opened by pulling on tab 50 on the strap 35.

The catheter can be attached to any desired administration set for the delivery of feeding formula or medications.

The anti-reflux valve 17 permits one-way infusion into the device, but prevents body fluids from escaping.

The valve can be opened at anytime to drain the device by opening cap 36 and inserting drainage tube 30.

Some physicians prefer other style distal tips such as pezzer type, conical type, mushroom type, or malecot type. These are all hollow bulbous types of tips which are deformable to be inserted or placed inside a body cavity, particularly the stomach.

Rigid obturators are used to stretch out these tips during insertion.

Anti-reflux valves can be incorporated in any one of these alternate style tips, and the device can readily be designed with any of these tips in mind.

As can be seen from FIG. 9 the device in its final form is a very low profile, close to the skin surface device. It also meets all of the objectives. Ease of placement, patient comfort, low cost, and the ability for the patient to lead a normal active life, are all advantages of this device.

While there is shown and described herein specific structures of the device, it will be apparent to anyone skilled in the art to make various modifications to the device without departing from the spirit and scope of the invention.

The invention, therefore, is not limited to particular forms or elements herein shown and described.

What is claimed:

1. An indwelling medical device wherein said device consists of:
   a flexible distal tip with an opening therein,
   a flexible tubular member with a lumen connected to the opening on the distal tip to form a fluid passageway between the tip and the tubular member to outside the body, said
   distal tip adapted to be located within the body and the tubular member proximal to the distal tip such that after placement a portion of the tubular member exists outside the body, said
   flexible tubular member having multiple engagement elements located on its outside surface, said
   engagement elements on the outside surface of the tubular member clearly visible outside the body after placement, and
   a separate external coupling incorporating at least one matching engagement element capable of selective engagement with at least one of said elements on the outside surface of the tubular member wherein said engagement takes place outside the body, the
   separate coupling further capable of being selectively positioned on the tubular member such that the coupling can rest close to the skin surface,
   a compression element capable of locking the coupling to the tubular member after selective positioning of the coupling on the tubular member, said
   compression element preventing engaged elements on both the coupling and the tubular member from disengagement such that the coupling and the tubular member become fixed together so that the external coupling prevents inward migration of the tubular member within the body.

2. An indwelling medical device of claim 1 wherein an anti-reflux valve is included in the distal tip.

3. An indwelling medical device of claim 1 wherein the tip is of the deformable mushroom or pezzer type.

4. An indwelling medical device of claim 1 wherein said tip is hollow and deformable.

5. An indwelling medical device of claim 1 wherein the anti-reflux valve is housed inside the lumen of the catheter.

6. An indwelling medical device of claim 1 wherein a closure plug is provided.

7. An indwelling medical device of claim 6 wherein the closure plug is attached to the external coupling.

8. An indwelling medical catheter for draining or infusion of fluids consisting of:
   a distal tip for positioning inside the body,
   an opening in said distal tip,
   an inner fluid passageway in said catheter connected to said distal tip, said
   passageway extending substantially the full length of the catheter from said distal tip to outside the body,
   an outer on said passageway wherein said outer wall extends outside the body and said outer wall incorporates a series of engagement elements wherein said elements also extend outside the body,
   an external bolster with at least one matching engagement element, said
   bolster capable of selective engagement with any of the engagement elements located on the outer wall of the passageway,
   a said bolster further capable of being adjustably positioned on said outer wall such that the external bolster rests close to the skin surface outside the body,
   a compression element capable of locking the bolster in place on the outer wall of the passageway, said
   compression element once in place in the locking mode preventing engaged elements between the bolster and outer wall from being disengaged to prevent slippage of the bolster on the outer wall of the passageway.

9. An indwelling medical catheter of claim 8 where said distal tip is a flexible element larger in diameter than the tubular member.

10. An indwelling medical catheter of claim 8 wherein said distal tip is a hollow member which is deformable.

11. An indwelling medical catheter of claim 8 wherein said distal tip opening is surrounded by a hollow member with at least one drainage hole.

12. The indwelling medical catheter of claim 8 wherein an anti-reflux valve is provided to prevent reflux of fluid from exiting the passageway to the outside of the body.

13. The indwelling medical catheter of claim 8 wherein an anti-reflux valve is housed within the distal tip.

14. The indwelling medical catheter of claim 8 including a closure plug to stop fluid from exiting the passageway.

15. The indwelling medical catheter of claim 8 wherein the distal tip is flexible and hollow and capable of being deformed and inserted inside the body using a rigid obturator.

16. An indwelling medical device wherein said device consists of:
   a flexible distal tip with an opening therein,
   a flexible hollow catheter proximal to said distal tip with an internal passageway connected to the opening on said distal tip,
   said passageway in direct fluid communication with the opening in said distal tip, said
   catheter further having a series of engagement elements progressively located on an outside wall of the catheter,
   at least a portion of the catheter including engagement elements extending outside the body after placement of the distal tip inside the body, a separate external coupling with an opening therein, said opening including matching engagement elements, said opening and said matching engagement elements cooperating with the engagement elements on the outside wall of the catheter to form an interlocking connecting between the coupling and the catheter, said coupling capable of engagement with any of the elements on the outside wall of the catheter such that the coupling can be positioned and engaged so that the coupling can rest close to the skin surface, a compression element in conjunction with the coupling such that the coupling can be locked in position with the catheter after compression of the element such that the coupling and catheter cannot be disengaged without relieving the compression element.

17. The indwelling medical device of claim 16 wherein the compression element is a pull tie.

18. The indwelling medical device of claim 16 wherein the engagement elements on the catheter wall are a series of saw teeth.

19. The indwelling medical device of claim 16 wherein an anti-reflux valve is included in the distal tip.

20. The indwelling medical device of claim 16 where said distal tip is hollow and deformable.

21. The indwelling medical device of claim 16 where said distal tip consists of at least one outwardly extending flange.

22. The indwelling medical device of claim 16 wherein said distal tip prevents outward migration of the catheter and said external coupling prevents inward migration of the catheter.

23. A gastrostomy feeding device comprising:
a distal tip with an opening therein,
a hollow catheter proximal to the distal tip connected to the distal tip and extending rearward therefrom,
a
hollow catheter lumen in direct fluid communication with the distal tip opening, said hollow catheter having an outside wall with a series of engagement elements which are clearly visible outside the body, said distal tip with outwardly extending retaining means, a said distal tip including retaining means adapted for contact with the inner wall of the stomach to prevent outward migration of the device after placement, and a separate external bolster with at least one matching engagement element capable of interlocking with said engagement elements which are clearly visible outside the body one the hollow catheter wall, said separate external bolster further capable of being selectively positioned on the hollow catheter such that the bolster can rest close to the skin surface while still engaged with the elements clearly visible outside the body on the hollow catheter, a compression element applying inward compressive force on the external bolster in the area of its said at least one matching engagement element to securely interlock the bolster to the hollow catheter to prevent inward migration of the catheter inside the body.

24. A gastrostomy feeding device of claim 23 wherein the distal tip retaining means is hollow and deformable.

25. A gastrostomy feeding device of claim 23 wherein an anti-reflux valve is positioned in the distal tip retaining means.

26. A gastrostomy feeding device of claim 23 wherein an anti-reflux valve is positioned in the hollow catheter lumen.

27. A gastrostomy feeding device of claim 23 wherein a dilator is attached to the proximal hollow catheter enabling placement of the device using the percutaneous endoscopic gastrostomy procedure.

28. A gastrostomy feeding device of claim 23 wherein the lumen of the hollow catheter can be connected to an administration set or connecting tube to deliver feeding formula.

29. A gastrostomy feeding device of claim 23 including a closure cap for the lumen of the hollow catheter.

30. A gastrostomy feeding device of claim 29 wherein the closure cap is pre-attached to the external bolster.

* * * * *